United States Patent [19]

Nokihara et al.

[11] Patent Number: 5,470,703
[45] Date of Patent: Nov. 28, 1995

[54] METHOD FOR PEPTIDE C-TERMINAL FRAGMENT SEQUENCE ANALYSIS AND APPARATUS FOR COLLECTING PEPTIDE FRAGMENT

[75] Inventors: Kiyoshi Nokihara; Rintaro Yamamoto, both of Kyoto, Japan

[73] Assignee: Shimadzu Corporation, Kyoto, Japan

[21] Appl. No.: 136,761

[22] Filed: Oct. 15, 1993

[30] Foreign Application Priority Data

Oct. 21, 1992 [JP] Japan ................................. 4-308197
Oct. 29, 1992 [JP] Japan ................................. 4-291022

[51] Int. Cl.⁶ ........................ C12Q 1/00; C12N 11/00; C12M 1/40
[52] U.S. Cl. .................. 435/4; 435/174; 435/180; 435/212; 435/287.3; 435/287.7; 435/288.1; 435/297.1; 435/289.1; 436/86; 436/89; 436/90; 436/162; 436/178; 436/810; 530/333; 530/334; 422/101; 422/102
[58] Field of Search .......................... 435/4, 174, 180, 435/212, 288, 294, 296, 313; 436/86, 89, 90, 162, 178, 810; 530/333, 334; 422/101, 102

[56] References Cited

U.S. PATENT DOCUMENTS 4,665,037  5/1987  Stolowitz ..................... 436/89
5,169,935  12/1992 Hoeger et al. ................ 530/328

FOREIGN PATENT DOCUMENTS 0217634   4/1987  European Pat. Off. .
0529504   3/1993  European Pat. Off. .
4005518   8/1991  Germany .
235600    9/1989  Japan .
WO92/03737 3/1992  WIPO .

OTHER PUBLICATIONS

Vath et al, *Chemical Abstract*, vol. 114, p. 808, Ref. #82527m, 1991 (Int. J. Mass Spectrom. Ion Process 1990, 100, 287–99).

Jahnen–Dechent et al, *Chemical Abstract*, vol. 115, 1991, p. 450, Ref. #45566y (Plant Mol. Biol. Rep. 1990, 8(2), 92–103).

Geysen et al, *Proc. Natl. Acad. Sci. USA*, vol. 81, pp. 3998–4002, Jul. 1984.

Houghten, *Proc. Natl. Acad. Sci. USA*, vol. 87, pp. 5131–5135, Aug. 1985.

Merrifield, Science, vol. 232, pp. 341–347 (1986).

*Primary Examiner*—Michael G. Wityshyn
*Assistant Examiner*—Abdel A. Mohamed
*Attorney, Agent, or Firm*—Birch, Stewart, Kolasch & Birch

[57] ABSTRACT

The present invention relates to a method for peptide C-terminal fragment sequence analysis, in which the fragment collection is carried out on an allylamine group-derivatized polymer membrane or on allylamine group-derivatized glass fiber filter paper; the collected C-terminal fragment is immobilized thereon using a water-soluble carbodiimide etc.; and the obtained immobilized product is subjected directly to amino acid sequence analysis. The present invention also relates to an apparatus for collecting a peptide fragment. According to the method of the present invention, peptides which are rich in hydrophobic groups in their C-terminus and are therefore difficult to trap with polyvalent ion carriers, currently used in the gas-phase sequencer, can be completely analyzed up to their C-terminus. Also, amino acid sequence analysis can be made even when the amount of C-terminal fragments is very small. In addition, since collection and immobilization of fragments can be done in the same bottle, the risks of contamination and mechanical loss are very low.

5 Claims, 4 Drawing Sheets

METHOD FOR PEPTIDE C-TERMINAL FRAGMENT SEQUENCE ANALYSIS AND APPARATUS FOR COLLECTING PEPTIDE FRAGMENT

BACKGROUND OF THE INVENTION

1. Field of the Invention

The present invention relates to a method for peptide C-terminal fragment sequence analysis wherein fragments are cleaved and collected from the carboxyl terminus (hereinafter referred to as the C-terminus) of a protein or peptide and subsequently analyzed for amino acid sequence, and to an apparatus for collecting a peptide fragment which can be used in the peptide fragment cleavage and collection process.

2. Discussion of the Related Art

Conventional methods for peptide C-terminal analysis include the hydrazinolysis method and the carboxypeptidase method. The carboxypeptidase method, based on the action of various kinds of carboxypeptidase to sequentially break peptide bonds from the carboxyl terminus of the polypeptide, has some drawbacks, such as complex operation, the requirement for a relatively large sample volume, and unreliable results of sequencing.

As a modified method free from these drawbacks, Japanese Patent Laid-Open No. 235600/1989 discloses a method wherein a peptide is cleaved with Lys-C specific cleavage enzyme, each resulting fragment is bound to a solid support having a functional group capable of reacting with the α-amino group and ε-amino group of the fragment to form a covalent bond, then the peptide bond between the α-amino terminal amino acid residue of each fragment and the amino acid residue adjacent thereto is cleaved by acid treatment, and a C-terminal peptide in a free form is collected. The same publication also discloses that the C-terminal peptide thus obtained can be used for amino acid sequence analysis by various methods of amino acid sequence analysis.

However, when this method is used for fragment collection, there are still several problems in the analysis of the amino acid sequence. Specifically, it is well-known that hydrophobic peptides of relatively short chains consisting of not more than about several 10 amino acids, particularly peptides having a hydrophobic amino acid at the C-terminus, are difficult to trap with polybrene or other polyvalent ion carriers used in the gas-phase protein sequencer, and sample wash-out is therefore likely to occur, which hampers the completion of amino acid sequence analysis.

Also, there has been no suitable peptide fragment collector developed for this process. Conventional collectors are configured, for example, as illustrated in FIG. 3. Specifically, reagents 31 and 32 are added to a sample loaded in a reactor (column) R to carry out cleavage or decomposition of the sample in the reactor, and the cleaved (decomposed) sample is dispensed to a recovery bottle 12 or a waste liquid bottle 13, both provided in the downstream of the reactor R.

In this case, switching between the recovery bottle 12 and the waste liquid bottle 13 is achieved by the operation of valve V. In FIG. 3, V1 represents a two-way valve and V2 and V3 respectively represent a three-way valve. Reagents 31 and 32 are supplied by the pressure of inert gas. In conventional collectors as exemplified above, the dispensing of the sample is achieved by valve operation and, therefore, contamination can occur when there is a dead volume in a valve.

Also, when using a reagent or a sample which precipitates upon drying, such as urea, it is undesirable to pass it through valves because precipitation occurs in the valves. Such limitative factors make it impossible to carry out a peptide cleaving reaction and collect peptide fragments using such conventional collectors.

Furthermore, when the reactor is packed with a packing material, the packing material can escape and cause damage downstream to the valves.

SUMMARY OF THE INVENTION

The object of the present invention is to solve the above problems, and provide a method for peptide C-terminal fragment analysis which allows complete and efficient analysis of amino acid sequence up to the C-terminus of the peptide, and an apparatus for collecting a peptide fragment which allows dispensing of sample and other fluids without using any valve.

Accordingly, the present invention relates to a method for peptide C-terminal fragment sequence analysis, comprising the steps of cleaving a peptide with Lys-C specific cleavage enzyme; reacting each resulting fragment with a solid support having a functional group capable of reacting with the α-amino group of each fragment and the ε-amino group of Lys to form a covalent bond therewith; cleaving the peptide bond between the α-amino acid residue of each fragment and the amino acid residue adjacent thereto by acid treatment; collecting a free carboxyl terminal (C-terminal) fragment having no ε-amino group; and analyzing for the amino acid sequence. The fragment collection in the above steps may be carried out on an allylamine group-derivatized polymer membrane or on allylamine group-derivatized glass fiber filter paper; the collected C-terminal fragment is immobilized on the polymer membrane or on the glass fiber filter paper using a water-soluble carbodiimide etc.; and the obtained immobilized product is subjected directly to amino acid sequence analysis.

The present invention also relates to an apparatus for collecting peptide fragments into a number of bottles set downstream of the reactor, comprising a branch pipe provided between the reactor and the bottles so as to separate the fluid from the reactor into a number of flow paths, and a means for applying gas pressure from the downstream of the branch pipe on the flow paths through which the fluid is not to be passed.

According to the method of the present invention, peptides which are rich in hydrophobic groups in their C-terminus and are therefore difficult to trap with polyvalent ion carriers, such as polybrene, currently used in the gas-phase sequencer, can be completely analyzed up to their C-terminus. Also, amino acid sequence analysis can be used even when the amount of C-terminal fragments is very small (not more than 10 pmol). In addition, since collection and immobilization of fragments can be done in the same bottle, the risks of contamination and mechanical loss are very low.

Further, the apparatus for collecting the peptide fragment (hereinafter referred to as the collector) of the present invention does not require valve operation, and therefore dead volume does not occur downstream of the reactor column. Accordingly, this collector is suitable for the method of the present invention because it is free from such problems as contamination.

BRIEF DESCRIPTION OF THE DRAWINGS

The present invention will become more fully understood from the drawings given hereinbelow which are given by way of illustration only, and thus, are not limitative of the present invention, and wherein.

Figure 2:
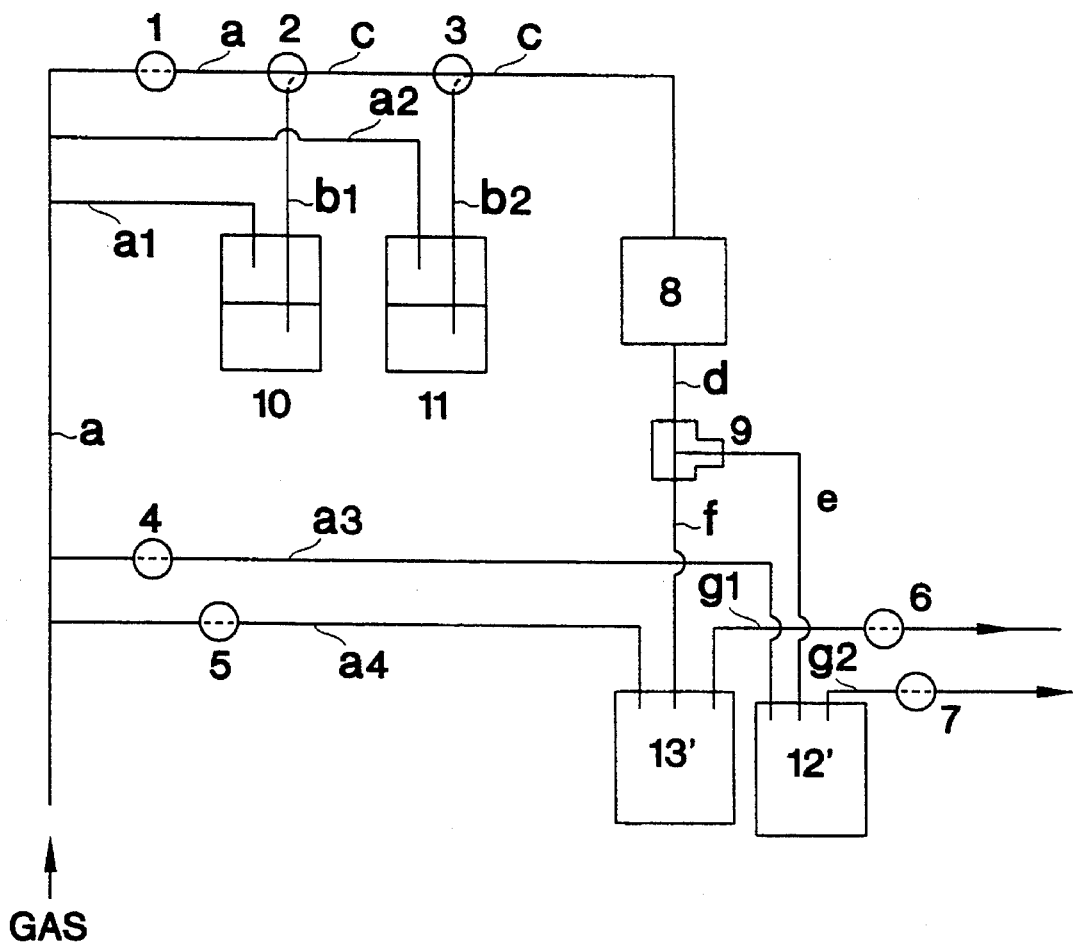
FIG. 2 is a schematic illustration of the apparatus used in the present invention.
Figure 3:
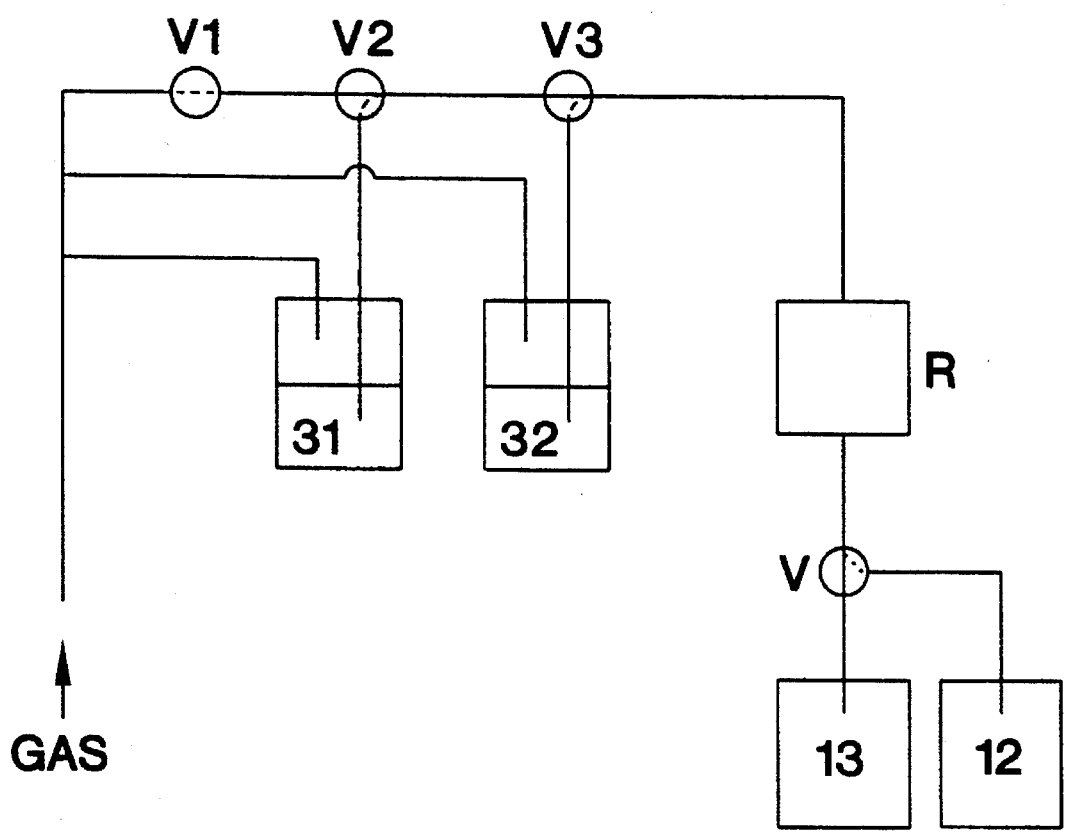
FIG. 3 is a schematic illustration of a conventional collector.
Figure 4:
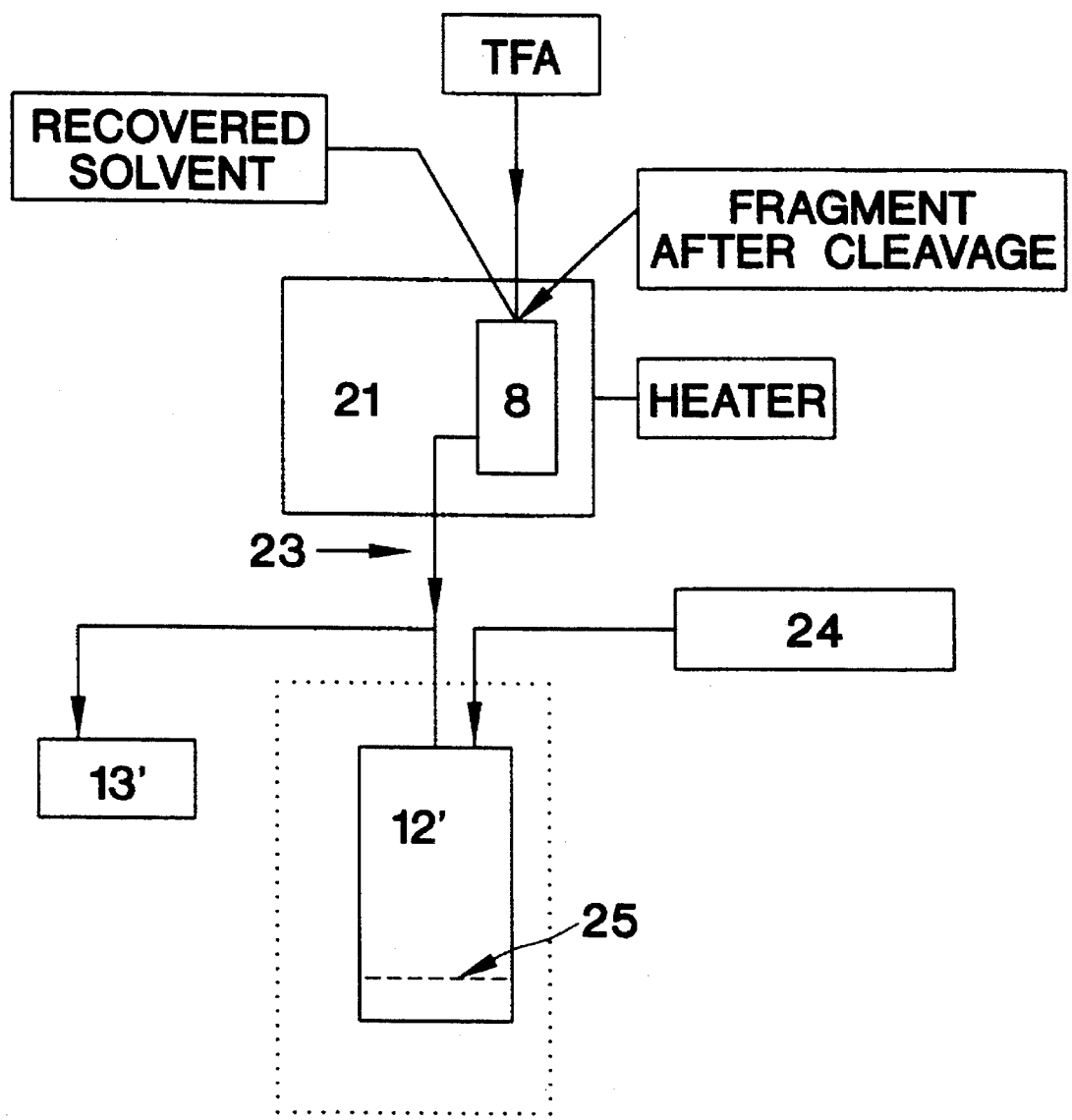
FIG. 4 is a schematic diagram of an apparatus for C-terminal fragment collection and immobilization in the present invention.

The reference numerals in FIGS. 2 through 4 denote the following elements:

Elements 2 and 3 are three-way valves, elements 1, 4, 5, 6 and 7 two-way valves, element 8 a reaction column, element 9 a manifold, elements 10 and 11 reagent reservoirs, elements 12 and 12', recovery bottles, elements 13 and 13' waste liquid bottles, element 21 a reaction vessel, element 23 a reaction mixture flow path, element 24 a $N_2$ purge line, element 25 a membrane, element 31 reagent 1, element 32 reagent 2, element a (a1, a2, a3 and a4) gas supply pipes, element b (b1 and b2) reagent supply pipes, element c a reagent supply flow path, element d a reaction mixture discharge flow path, element e a recovery flow path, element f a waste liquid flow path, element g (g1 and g2) exhaust pipes, element R a reactor, element $V_1$ a two-way valve, and elements V, $V_2$ and $V_3$ three-way valves.

DETAILED DESCRIPTION OF THE INVENTION

In the present invention, Lys-C specific cleavage enzyme is defined as an enzyme which specifically cleaves peptide bonds at the C-terminal side of Lys residues in the peptide. Such enzymes include API (*Achromobacter lyticus* protease I) and Endoproteinase Lys-C (trade name, manufactured by Boehringer Mannheim), but are not subject to limitation, as long as they exhibit the above-described action.

In the present invention, a functional group capable of reacting with the amino group to form a covalent bond therewith is exemplified by the imide group, the aldehyde group, the cyano group, the acetyl group, the succinyl group, the maleyl group and the isothiocyanate group, with preference given to the isothiocyanate group from the viewpoint of specific reactivity with the amino group and specific post-binding cleavage. Also, the solid support having such a functional group is a solid carrier, made of a material such as porous glass, silica gel or polystyrene, and is exemplified by DITC-polystyrene.

Although the acid used for acid treatment in the present invention is subject to no limitation, preference is given to trifluoroacetic acid (TFA) because of its high volatility, high reactivity and low prevalence of side reactions.

Figure 1:
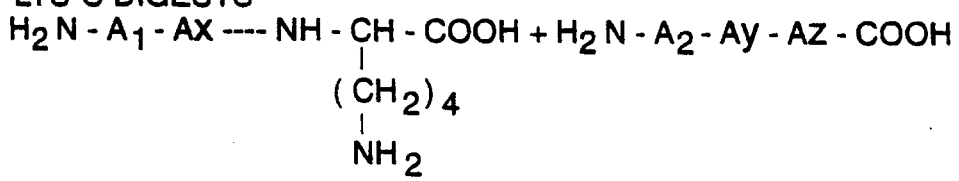
FIG. 1 is a schematic illustration in the chemical procedure of C-terminal fragment peptide separation of the present invention.
Figure 1:
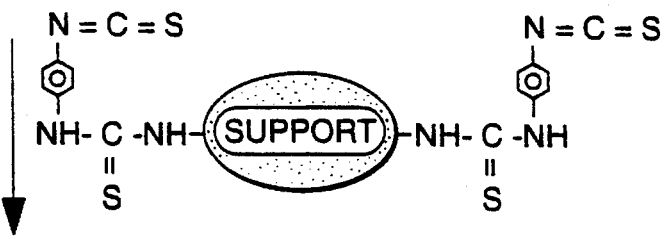
Figure 1:
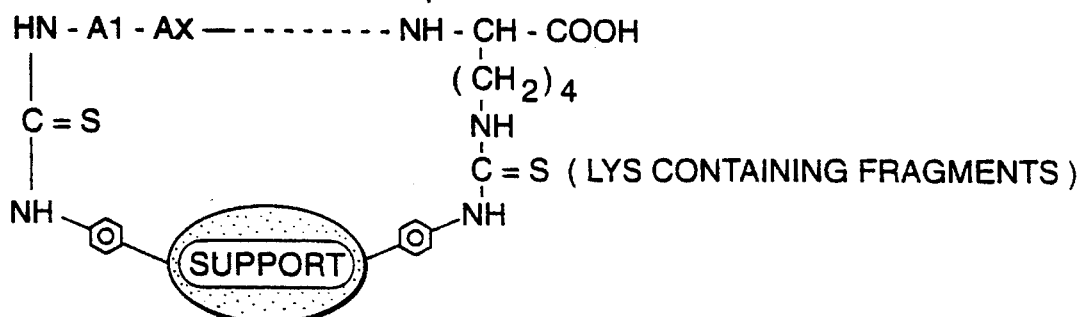
Figure 1:
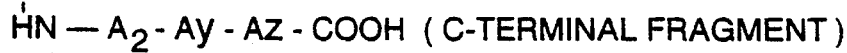
Figure 1:
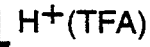
Figure 1:
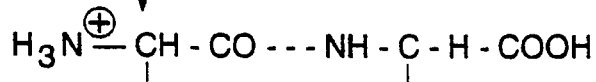
Figure 1:
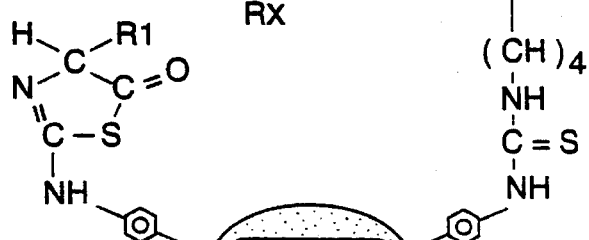
Figure 1:
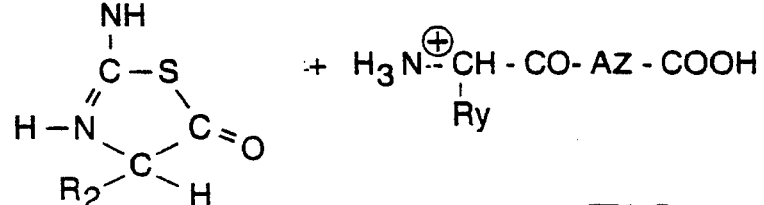

The chemical procedure of C-terminal fragment peptide separation in the present invention is illustrated in FIG. 1.

In the present invention, the polymer membrane derivatized with the amino group is exemplified by the allylamine membrane PVDF (polyvinylidene difluoride) (Sequelon-AA™, manufactured by MilliGen). The carrier glass fiber derivatized with the amino group as a material for the glass fiber filter paper is exemplified by aminopropyl glass and aminophenyl glass. The polymer membrane size, e.g., preferably 8 to 10 mm in diameter, is subject to no limitation, as long as the polymer membrane can be attached into the recovery bottle for fraction collection and can be housed in the reaction chamber cartridge of the sequencer.

Next, the peptide fragment collector of the present invention is hereinafter described in detail.

The reactor used in the peptide fragment collector of the present invention is exemplified by a reactor housing a solid support to which the amino terminus of peptide has been bound. However, this is not limitative; various reactors such as liquid chromatograph separation columns and peptide synthesizer reaction columns can be used for this purpose.

A number of bottles set downstream of the reactor can be used both for recovered liquid and for waste liquid. It is also possible to employ an apparatus wherein recovery bottles are set on a turn table and are rotated in sequence.

The branch pipe may be of any type, as long as it can divide the flow of the fluid to run from the reactor to the flow path of each bottle, and it is exemplified by a manifold.

The pressure applying means serves to apply pressure, from the downstream of the branch pipe, upon the flow path of any one of the bottles to keep the pressure in the flow path higher than the pressure of the fluid flowing from the reactor, and it is exemplified by an inert gas cylinder equipped with a regulator. Pressure may be applied onto one or more flow paths to which the fluid is not to be flown, i.e., the flow paths leading to the bottles from which the fluid is not to be collected.

As stated above, the use of the peptide fragment collector of the present invention makes it possible to flow the fluid only to selected flow path(s) by applying gas pressure, in the opposite direction to the flow, on the flow path through which the fluid is not to be flowed.

EXAMPLES

The present invention is hereinafter described in more details by means of the following working examples, but the present invention is not limited by them.

Example 1

FIG. 2 is a schematic illustration of a peptide fragment collector, in which the numerical symbol 8 represents a reaction column (a reactor). The reaction column is packed with a solid support having a functional group (for instance, a porous glass having the isothiocyanate group introduced therein) bound with amino acid residues treated with enzyme (for instance, lysyl endopeptidase).

Upstream of the reaction column 8 are provided the reagent reservoirs 10 and 11. In the case of, for example, a peptide C-terminal fragment collector, the reagent reservoirs 10 and 11 contain a detergent and a cleaving agent (for instance, trifluoroacetic acid), respectively. These reagent reservoirs 10 and 11 are tight bottles, each having two pipes (a1 and b1/a2 and b2), one for gas supply (a1, a2) and the other for reagent supply (b1, b2). Reagent supply pipes b1 and b2 are connected to a reagent flow path c via three-way valves 2 and 3.

Gas supply pipes a1 and a2 are connected to a pipe a from an inert gas source (not illustrated). The pipe a is connected to a reagent supply flow path c via a two-way valve 1 to allow the direct application of gas pressure on the reaction column 8.

In the downstream of the reaction column 8 is provided a manifold 9, to which a reaction mixture discharge flow path d, a recovery flow path e and a waste liquid flow path f are separately connected.

One end of the recovery flow path e and one end of the waste liquid flow path f are housed in a closed type recovery bottle 12' and a closed type waste liquid bottle 13', respectively. The recovery bottle 12' and the waste liquid bottle 13' house gas supply pipes a3 and a4 and exhaust pipes g2 and g1, respectively. The gas supply pipes a3 and a4 are connected to pipe a from an inert gas source (not illustrated) via two-way valves 4 and 5 in the same manner as above. In FIG. 2, numerical symbols 6 and 7 represent a two-way valve.

With this configuration, waste liquid is discharged as follows:

Step 1: For sending the discharge from the reaction column 8 to the waste liquid bottle 13', open the valves 4 and 6 and close the valves 5 and 7. The gas from the inert gas source passes the two-way valve 4 and enters in the gas supply pipe a3 and then the recovery bottle 12', after which it passes via the recovery flow path e, the manifold 9 and then the waste liquid flow path f and enters into the waste liquid bottle 13'. The gas entering in the waste liquid bottle 13' is discharged through the exhaust pipe g1 and the two-way valve 6.

Step 2: When the three-way valve 2 is opened (indicated by dotted line in FIG. 2) and the three-way valve 3 is closed (indicated by solid line in FIG. 2) under the above condition, the liquid in the reagent reservoir 10 is supplied to the reaction column 8 through the reagent supply pipe b1 and then the reagent supply flow path c by the pressure on the surface, after which it reaches the manifold 9 through the reaction mixture discharge flow path d. Because the manifold 9 is under pressure from the recovery bottle 12', all the liquid reaching the manifold 9 enters into the waste liquid bottle 13'.

Step 3: Following step 2, close the three-way valve 2 and open the two-way valve 1. Supply of the liquid in the reagent reservoir 10 is stopped, the gas pressure from the inert gas source is applied directly to the reaction column 8, and all the liquid from the reaction column 8 enters in the waste liquid bottle 13'.

Next, the liquid is recovered as follows:

Step 4: First, open the valves 5 and 7, and close the valves 4 and 6. The gas from the inert gas source passes the two-way valve 5 and enters in the gas supply pipe a4 and then the waste liquid bottle 13', after which it passes via the waste liquid flow path f, the manifold 9 and then the recovery flow path e and enters into the recovery bottle 12'. The gas entering in the recovery bottle 12' is discharged through the exhaust pipe g2 and the two-way valve 7.

Step 5: When the three-way valve 3 is opened under the above condition, the liquid in the reagent reservoir 11 is supplied to the reaction column 8 through the reagent supply pipe b2 and then the reagent supply flow path c by the pressure on the surface, after which it reaches the manifold 9 through the reaction mixture discharge flow path d. Because the manifold 9 is under pressure from the recovery bottle 13', all the liquid reaching the manifold 9 enters into the recovery bottle 12'.

Step 6: Following step 5, close the three-way valves 2 and 3 and open the two-way valve 1. Supply of the liquid in the reagent reservoir 11 is stopped, the gas pressure from the inert gas source is applied directly to the reaction column 8, and all the liquid from the reaction column 8 enters in the recovery bottle 12'.

With the configuration described above, the liquids in the reagent reservoirs 10 and 11 are supplied directly to the reaction column via the flow path c. Alternatively, a measuring tube and liquid sensor may be provided between the three-way valve 3 and the reaction column 8 to allow constant-volume sampling.

According to the peptide fragment collector of the present invention, it is possible to provide a flow path system where there is no dead volume downstream of the reaction column, because fluid can be dispensed without using a valve.

In addition, the present invention does not limit the reagents to be used, and it is also possible to provide a flow path system which can endure accidental leakage of packing material from the reaction column etc.

Example 2

The method for peptide C-terminal fragment analysis of the present invention is hereinafter described with reference to FIG. 4.

FIG. 4 is a schematic diagram of an apparatus for C-terminal fragment collection and immobilization in the present invention.

First, the desired peptide was cleaved with, for example, Lys-C specific cleavage enzyme, at a reaction temperature of 37° C., after which the resulting fragments were reacted with a solid support having a functional group capable of reacting with the α-amino group thereof and the ε-amino group of Lys to form a covalent bond therewith (e.g., DITC polystyrene). The coupling reaction between the solid support and the peptide fragments resulting from cleavage by the above enzyme treatment was carried out at a reaction temperature of 48° C. to 50° C. for about 1 hour. This reaction is preferably carried out in the reaction column 8 arranged in a reaction vessel 21 equipped with a heater to allow optimum reaction conditions. After completion of the coupling reaction, the solid support was washed and subjected to an acid treatment. The acid treatment was carried out with trifluoroacetic acid (TFA) in a nitrogen atmosphere at a reaction temperature of 30° C. to 50° C., preferably at 48° C., for 15 minutes.

After completion of the reaction, the TFA was removed by drying. Next, the reaction mixture was recovered into the cylindrical recovery bottle 12' having a polymer membrane 25 in its bottom portion (or glass fiber filter paper), whose membrane size was suitable for the sequencer reactor size of the analyzer used for the subsequent amino acid sequence analysis. While the reaction mixture was being sent to the recovery bottle 12' through a reaction mixture flow path 23, the recovery bottle 12' was purged with $N_2$ gas from a $N_2$ purge line 24, whereby the reaction solution (recovered solution), in which nothing other than peptide C-terminal fragments has been dissolved, is evaporated to dryness. The material for the recovery bottle 12' was polypropylene or other material which is unlikely to cause non-specific adsorption.

In the above processes, the peptide C-terminal fragment collector of Example 1 can be used.

While keeping the membrane 25 in the recovery bottle 12', 30 to 50% acetonitrile (not more than 30 μl) was added to the recovery bottle 12'. The recovery bottle 12' was placed in a heat block and heated at 55° C. After the temperature of the recovery bottle 12' was returned to a room temperature, 15 μl of a reagent solution [0.1M 4-morpholineethanesulfonic acid (MES), pH 5.0, 15% acetonitrile, 10 mg/ml water-soluble carbodiimide (EDC)] was added. The recovery bottle was allowed to stand for 20 minutes, and then the membrane 25 was taken out and washed with acetonitrile and dried. Thereafter, it was applied to the sequencer.

According to the method of the present invention, the risk of contamination can be minimized, because amino acid sequence analysis is initiated by directly placing the polymer membrane or glass fiber filter paper to which C-terminal fragments have been immobilized by the method described above in the reactor of an amino acid sequence analyzer (e.g., a gas-phase sequencer).

The present invention being thus described, it will be obvious that the same may be varied in many ways. Such variations are not to be regarded as a departure from the modifications as would be obvious to one skilled in the art are intended to be included with in the scope of the following claims.

What is claimed is:

1. A method for peptide C-terminal fragment sequence analysis comprising the steps of cleaving a peptide with Lys-C specific cleavage enzyme; reacting each resulting fragment with a solid support having a functional group capable of reacting with an $\alpha$-amino group of each fragment and an $\epsilon$-amino group of Lys to form a covalent bond therewith; cleaving a peptide bond between the $\alpha$-amino acid residue of each fragment and an amino acid residue adjacent thereto by acid treatment to give a free C-terminal fragment having no $\epsilon$-amino group; collecting the free C-terminal fragment on an amino group-derivatized polymer membrane or on amino group-derivatized glass fiber filter paper; immobilizing the collected C-terminal fragment on the polymer membrane or on the glass fiber filter paper; and subjecting the obtained immobilized product directly to amino acid sequence analysis.

2. The method according to claim 1, wherein the polymer membrane is allylamine group-derivatized polymer membrane.

3. The method according to claim 2, wherein the allylamine group-derivatized polymer membrane is polyvinylidene difluoride membrane.

4. The method according to claim 1, wherein the glass fiber filter paper is made of aminopropyl glass or aminophenyl glass.

5. The method according to claim 1, wherein the immobilization of the collected C-terminal fragment is carried out using a water-soluble carbodiimide.

* * * * *